(12) United States Patent
Brown

(10) Patent No.: US 6,630,173 B2
(45) Date of Patent: Oct. 7, 2003

(54) NAPHTHALIMIDE COMPOSITIONS AND USES THEREOF

(75) Inventor: Dennis M. Brown, Menlo Park, CA (US)

(73) Assignee: Chemgenex Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 09/834,177

(22) Filed: Apr. 12, 2001

(65) Prior Publication Data

US 2002/0025916 A1 Feb. 28, 2002

Related U.S. Application Data

(60) Provisional application No. 60/197,103, filed on Apr. 12, 2000.

(51) Int. Cl.$^7$ .......................... A61K 31/44; A61K 33/24
(52) U.S. Cl. ......................................... 424/649; 514/296
(58) Field of Search ................................ 514/296, 246; 424/649

(56) References Cited

U.S. PATENT DOCUMENTS 5,420,137 A 5/1995 Brana et al.

FOREIGN PATENT DOCUMENTS

WO    WO 01/68098 A2    9/2001

OTHER PUBLICATIONS

Ajani, J.A. et al., "In vitro activity of amonafide against primary human tumors compared with the activity of standard agents." Invest New Drugs. 1988 Jun.;6(2):79–85.

Asbury, R.F. et al., "A Gynecologic Oncology Group phase II study of amonafide (NSC #308847) in squamous cell carcinoma of the cervix." Am J Clin Oncol. 1994 Apr.;17(2):125–8.

Bernges, F. and Zeller, W.J. "Combination effects of poly-(ADP–ribose) polymerase inhibitors and DNA–damaging agents in ovarian tumor cell lines—with special reference to cisplatin." J Cancer Res Clin Oncol. 1996;122(11):665–70.

Cobb, P.W., et al., "Activity of DMP 840, a new bis–naphthalimide, on primary human tumor colony–forming units," J Natl Cancer Inst. 1994 Oct. 5;86(19):1462–5.

Costanza, M.E. et al., "Safety and efficacy of using a single agent or a phase II agent before instituting standard combination chemotherapy in previously untreated metastatic breast cancer patients: report of a randomized study—Cancer and Leukemia Group B 8642." J Clin Oncol. 1999 May;17(5):1397–406.

Costanza, M.E. et al., "Amonafide: An active agent in the treatment of previously untreated advanced breast cancer—a cancer and leukemia group B study (CALGB 8642)." Clin Cancer Res. 1995 Jul.;1(7):699–704.

Evans. W.K. et al., "Phase II study of amonafide: results of treatment and lessons learned from the study of an investigational agent in previously untreated patients with extensive small–cell lung cancer." J Clin Oncol. 1990 Mar.;8(3):390–5.

Gallion, H.H. et al., "Phase II trial of amonafide in previously treated patients with advanced ovarian cancer: a Southwest Oncology Group study." Gynecol Oncol. 1992 Aug.;46(2):230–2.

Hayes, D.F. et al., "Treatment of metastatic breast cancer: present and future prospects."Semin Oncol. 1995 Apr.;22(2 Suppl 5):5–19; discussion 19–21.

Innocenti, F., "Pharmacogenetics: a tool for individualizing antineoplastic therapy." Clin Pharmacokinet. 2000 Nov.;39(5):315–25.

Pérez, J.M., et al., "Combined effect of platination and intercalation upon DNA binding of novel cytotoxic Pt–bis-(naphthalimide) complexes." J Med Chem. 1999 Dec. 30;42(26):5482–6.

Wong, K. and Henderson, I.C. "Management of metastatic breast cancer." World J Surg. 1994 Jan.–Feb.; 18(1):98–111.

*Primary Examiner*—Jerome D. Goldberg
(74) *Attorney, Agent, or Firm*—Richard F. Trecartin; Dorsey & Whitney LLP

(57) ABSTRACT

A method of treatment of a host with a cellular proliferative disease, comprising contacting the host with a naphthalimide and an antiproliferative agent, each in an amount sufficient to modulate said cellular proliferative disease, is described. In some embodiments, the naphthalimide comprises amonafide (5-amino-2-[2-(dimethylamine)ethyl]-1H-benz[de-]isoquinoline-1,3-(2H)-dione). Antiproliferative agents of the invention comprise alkylating agents, intercalating agents, metal coordination complexes, pyrimidine nucleosides, purine nucleosides, inhibitors of nucleic acid associated enzymes and proteins, and agents affecting structural proteins and cytoplasmic enzymes. The invention comprises the described methods as well as compositions comprising a naphthalimide and an antiproliferative agent.

9 Claims, 3 Drawing Sheets

Amonafide:
$R_1 = NH_2$
$R_2 =$

NAPHTHALIMIDE COMPOSITIONS AND USES THEREOF

This application claims the benefit of U.S. Provisional Application No. 60/197,103, filed Apr. 12, 2000.

FIELD OF THE INVENTION

The technical field of the invention is the use of naphthalimides with antiproliferative agents to treat a host with a cellular proliferative disease.

BACKGROUND OF THE INVENTION

There is considerable interest in modulating the efficacy of currently used antiproliferative agents to increase the rates and duration of antitumor effects associated with conventional antineoplastic agents.

Conventional antiproliferative agents used in the treatment of cancer are broadly grouped as (1) chemical compounds which affect the integrity of nucleic acid polymers by binding, alkylating, inducing strand breaks, intercalating between base pairs or affecting enzymes which maintain the integrity and function of DNA and RNA; (2) chemical agents that bind to proteins to inhibit enzymatic action (e.g., antimetabolites) or the function of structural proteins necessary for cellular integrity (e.g., antitubulin agents). Other chemical compounds that have been identified to be useful in the treatment of some cancers include drugs which block steroid hormone action for the treatment of breast and prostate cancer, photochemically activated agents, radiation sensitizers, and protectors.

Of special interest to this invention are those compounds that directly affect the integrity of the genetic structure of the cancer cells. Nucleic acid polymers such as DNA and RNA are prime targets for anticancer drugs. Alkylating agents such as nitrogen mustards, nitrosoureas, aziridine containing compounds directly attack DNA. Metal coordination compounds such as cisplatin and carboplatin similarly directly attack the nucleic acid structure resulting in lesions that are difficult for the cells to repair which, in turn, can result in cell death. Other nucleic acid affecting compounds include anthracycline molecules such as doxorubicin, which intercalates between the nucleic acid base pairs of DNA polymers, bleomycin, which causes nucleic acid strand breaks, fraudulent nucleosides such as pyrimidine and purine nucleoside analogs, which are inappropriately incorporated into nucleic acid polymer structures and ultimately cause premature DNA chain termination. Certain enzymes that affect the integrity and functionality of the genome can also be inhibited in cancer cells by specific chemical agents and result in cancer cell death. These include enzymes that affect ribonucleotide reductase (e.g., hydroxyurea, gemcitabine), topoisomerase I (e.g., camptothecin) and topoisomerase II (e.g., etoposide).

One of the most broadly used of these DNA targeted anticancer drugs is cisplatin (cis-diamminedichloroplatinum II, CDDP). This compound is active against several human cancers including testicular, small-cell lung, bladder, cervical and head and neck cancer.

Although the clinical activity of currently approved antiproliferative agents against many forms of cancers can be shown, improvements in tumor response rates, duration of response and ultimately patient survival are still sought. The invention described herein demonstrates the novel use of the naphthalimides and analogs thereof, including amonafide, which can potentiate the antitumor effects of chemotherapeutic drugs, in particular, agents affecting the integrity of nucleic polymers such as DNA.

SUMMARY OF THE INVENTION

Methods and compositions are provided for the treatment of a host having a cellular proliferative disease, particularly a neoplasia. In the subject methods, pharmaceutically acceptable naphthalimide and an antiproliferative agent are administered in an amount sufficient to modulate the cellular proliferative disease.

DETAILED DESCRIPTION OF THE FIGURES

DETAILED DESCRIPTION OF THE INVENTION

Methods and compositions are provided for the treatment of a host with a cellular proliferative disease, particularly a neoplasia. In the subject methods, a pharmaceutically acceptable naphthalimide is administered, preferably systemically, in conjunction with an antiproliferative agent to improve the anticancer effects. In a preferred embodiment, the naphthalimide provides a chemopotentiator effect.

The agents are provided in amounts sufficient to modulate a cellular proliferative disease. In one embodiment, modulation of a cellular proliferative disease comprises a reduction in tumor growth. In another embodiment, modulation of a disease comprises inhibition of tumor growth. In another embodiment, modulation of a cellular proliferative disease comprises an increase in tumor volume quadrupling time (described below). In another embodiment, modulation of a cellular proliferative disease comprises a chemopotentiator effect. In another embodiment, modulation of a disease comprises a chemosensitizing effect. In other embodiments, modulation of a disease comprises cytostasis. In still other embodiments, modulation of a disease comprises a cytotoxic effect.

A chemical agent is a "chemopotentiator" when it enhances the effect of a known antiproliferative drug in a more than additive fashion relative to the activity of the chemopotentiator or antiproliferative agent used alone. In some cases, a "chemosensitizing" effect may be observed. This is defined as the effect of use of an agent that if used alone would not demonstrate significant antitumor effects but would improve the antitumor effects of an antiproliferative agent in a more than additive fashion than the use of the antiproliferative agent by itself.

As used herein, the term "naphthalimide" includes all members of that chemical family including benzisoquinolinedione and analogs thereof. The naphthalimide family is defined by chemical structure as depicted in FIG. 1.

Figure 1:
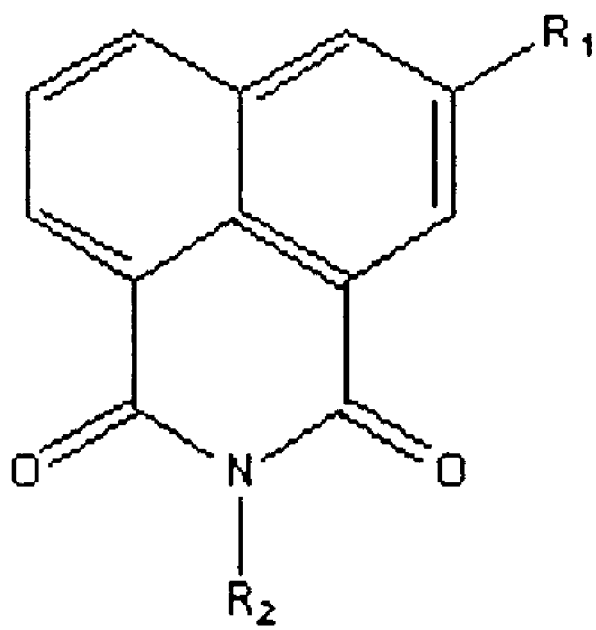
FIG. 1 depicts the general structure of a naphthalimide analog. $R_1$ and $R_2$ represent substitution groups. The structures of $R_1$ and $R_2$ for the naphthalimide analog, amonafide, are shown.
Figure 1:
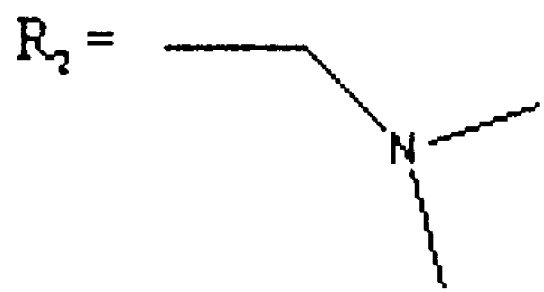

A naphthalimide analog is further defined but not limited to substituent changes in $R_1$ and $R_2$ (FIG. 1). Examples of $R_1$ and $R_2$ include those listed in Table 1. In a preferred embodiment, a naphthalimide analog has the structure of amonafide, shown in FIG. 2.

TABLE 1

| Group | Substitution | Length |
| --- | --- | --- |
| $R_1$ | Alkyl | $C_1 \to C_5$ |
|  | Amino |  |
|  | Nitro |  |

TABLE 1-continued

| Group | Substitution | Length |
|---|---|---|
| | Cyano | |
| | Alkoxy | $OC_1 \rightarrow OC_5$ |
| | Hydrogen | |
| $R_2$ | Alkyl | $C_1 \rightarrow C_5$ |

Figure 2:
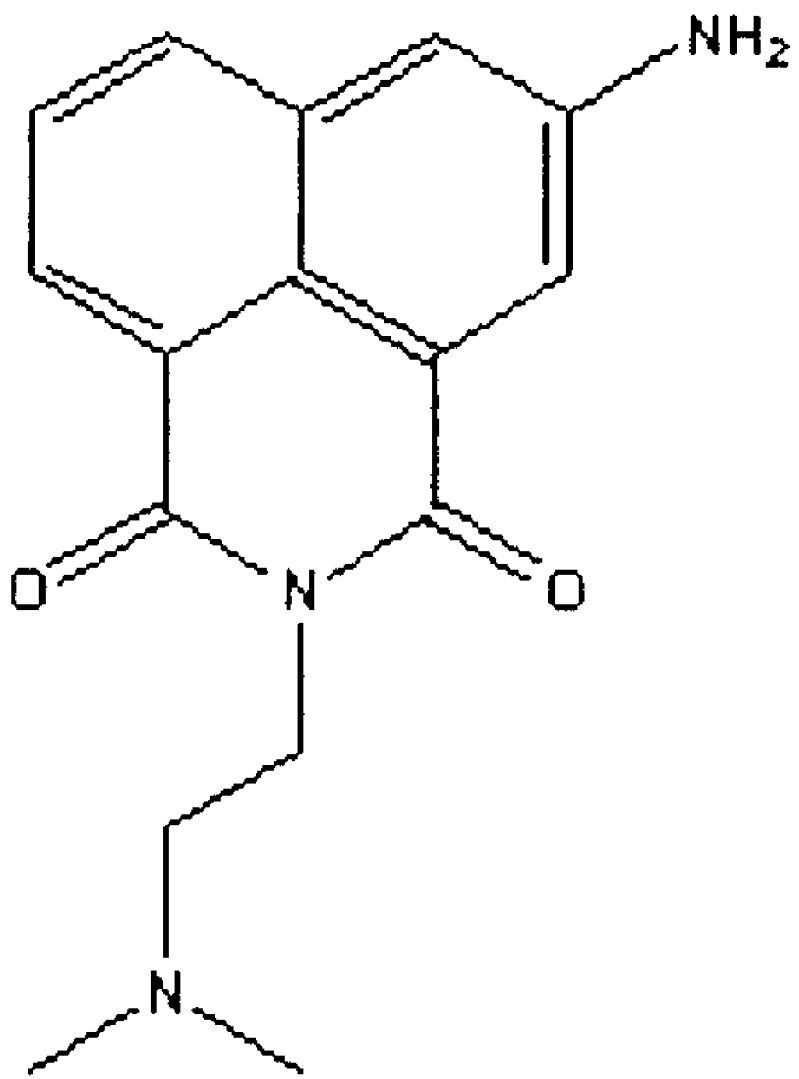
FIG. 2 depicts the structure of the naphthalimide analog, amonafide.
Figure 3:
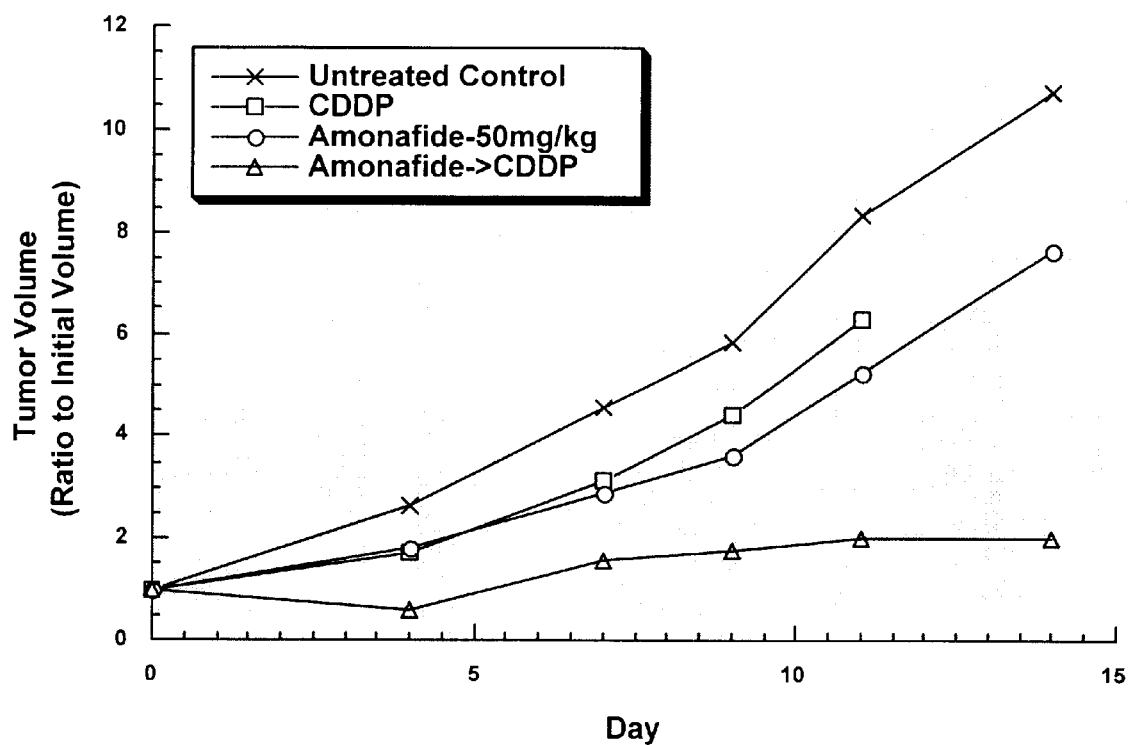
FIG. 3 shows tumor growth delay, as tumor volume on days after treatment with the naphthalimide analog, amonafide, amonafide followed by CDDP, or CDDP alone.

A naphthalimide analog is a further chemical refinement. A specific example of a naphthalimide analog is amonafide which is also known by the following chemical synonyms: Nafidamide; Benzisoquinolinedione; 5-amino-2-[(dimethylamine)ethyl]-1H-benz[de-]isoquinoline-1,3-(2H)-dione (FIG. 2).

As used herein, antiproliferative agents are compounds which induce cytostasis or cytotoxicity. "Cytostasis" is the inhibition of cells from growing while "cytotoxicity" is defined as the killing of cells.

Specific examples of antiproliferative agents include: antimetabolites, such as methotrexate, 5-fluorouracil, gemcitabine, cytarabine, pentostatin, 6-mercaptopurine, 6-thioguanine, L-asparaginase, hydroxyurea, N-phosphonoacetyl-L-aspartate (PALA), fludarabine, 2-chlorodeoxyadenosine, and floxuridine; structural protein agents, such as the vinca alkaloids, including vinblastine, vincristine, vindesine, vinorelbine, paclitaxel, and colchicine; agents that affect NF-κB, such as curcumin and parthenolide; agents that affect protein synthesis, such as homoharringtonine; antibiotics, such as dactinomycin, daunorubicin, doxorubicin, idarubicin, bleomycins, plicamycin, and mitomycin; hormone antagonists, such as tamoxifen and luteinizing hormone releasing hormone (LHRH) analogs; nucleic acid damaging agents such as the alkylating agents mechlorethamine, cyclophosphamide, ifosfamide, chlorambucil, dacarbazine, methylnitrosourea, semustine (methyl-CCNU), chlorozotocin, busulfan, procarbazine, melphalan, carmustine (BCNU), lomustine (CCNU), and thiotepa, the intercalating agents doxorubicin, dactinomycin, daurorubicin and mitoxantrone, the topoisomerase inhibitors etoposide, camptothecin and teniposide, and the metal coordination complexes cisplatin and carboplatin.

The following examples are offered by way of illustration and not by way of limitation.

EXAMPLE 1

Chemopotentiation of Cisplatin by Amonafide

Transplantable experimental murine fibrosarcomas ($2 \times 10^5$ RIF-1 cells) were grown intradermally in the flanks of 3 month old female C3H mice (Charles River, Holister, Calif.). When the tumors reached a volume of approximately 100 $mm^3$, the mice were randomly assigned to each experimental group (4 mice per group).

The experimental compositions were prepared as described in Table 2.

TABLE 2

| Agent | Dose | Solvent | Supplier |
|---|---|---|---|
| Amonafide | 50 mg/kg | DMSO | NCI |
| Cisplatin | 4 mg/kg | Water for injection | David Bull Labs |

The chemopotentiator, amonafide, was obtained from NCI and was made to the appropriate concentration in DMSO. Cisplatin (David Bull Laboratories—Mulgrave, Australia, lot. 5201844x) was made to the appropriate concentration in water for injection. The compositions were injected systemically (i.e., intraperitoneally, i.p.), in a volume of 100 microliters. For the treatment of group 3, the chemopotentiator, amonafide, was injected 30 minutes prior to the injection of cisplatin. After treatment, the growth of the tumors was monitored three times per week by caliper measurements of three perpendicular diameters of the tumor and calculation of tumor volume from the formula:

$$V = \pi/6 \times D_1 \times D_2 \times D_3,$$

where $D_{1-3}$ is in mm.

The tumors were followed until they reached a size of four times their day zero treatment volume (TVQT), or up to 30 days after treatment, whichever came first. The data is expressed as the "tumor volume quadrupling time" (TVQT) mean and as the "delay." Mean TVQT is the mean days required for individual tumors to grow to four times the tumor volume at the initial treatment day. The "delay" is the median of days required for a tumor to grow to four times the mean size of the treated group, minus the median of days required to grow to four times the mean size of the control group. The data is also expressed as the ratio of the tumor volume quadrupling time of the treated tumor over the untreated control group (TVQT/CTVQT). Increasing values of this ratio indicate increased antitumor response.

The data is presented in Table 3 below and in FIG. 2.

TABLE 3

| Group | Treatment | Dose (mg/kg) | Mean TVQT ± S.E. | TVQT/ CTVQT | Median (TVQT) | Delay (Days) |
|---|---|---|---|---|---|---|
| 1 | Untreated Control | — | 6.3 ± 0.3 | 1.0 | 6 | 0.00 |
| 2 | Amonafide | 50 | 9.7 ± 0.6 | 1.5 | 9.0 | 2.94 |
| 3 | Amonafide⇒ Cisplatin | 50 ⇒ 4 | 17.9 | 2.8 | 17.9 | 11.81 |
| 4 | Cisplatin | 4 | 8.4 ± 0.3 | 1.3 | 8.1 | 2.10 |

The arrow (⇒) in Group 3 indicates administration 30 minutes following administration of amonafide.

The results of Table 3 indicate that the antiproliferative activity of cisplatin is enhanced by the use of the chemopotentiator, amonafide in that a more than additive effect was observed when both compounds were used to treat the tumor bearing mice (group 3) in comparison to the use of cisplatin alone (group 4) or amonafide alone (group 2).

EXAMPLE 2

Effect of Amonafide, Alone and in Combination with Other Chemotherapeutics on RIF-1 Tumor Growth in C3H Mice The RIF-1 murine fibrosarcoma tumor model was used to evaluate the antitumor activity of amonafide, alone and and in combination with various antiproliferative agents. The antiproliferative agents used include those that affect nucleic acid (e.g., DNA) integrity (e.g., cisplatin, etoposide, 5-fluorouracil), agents that affect structural or cytoplasmic proteins or their synthesis (e.g., homoharringtonine, paclitaxel, vinblastine, colchicine, curcumin or parthenolide).

Amonafide-NCI was obtained from NCI as a powder. Amonafide-Penta was obtained from Penta Biotech (Union City, Calif.), Lot No.039-01, as a powder. Cisplatin for Injection, USP, was obtained from David Bull Labs (Mulgrave, Australia), Lot No.5201844x, as a lypholized powder. Paclitaxel was obtained from Bristol Myers Squibb Co. (Princeton, N.J.), Lot No. 9J16241, exp. September 2001, prediluted to 6 mg/mL in Cremaphor/EL. Vinblastine was obtained from Bedford Labs (Bedford, Ohio), Lot No.112647, as a lypholized powder. Etoposide was obtained from Pharmacia (Kalamazoo, Mich.), Lot No. ETA013, exp. May 1999, as a liquid prediluted to 20 mg/mL. 5-Fluorouracil was obtained from Pharmacia (Kalamazoo, Mich.), Lot No.FFA191, exp. July 2000, as a liquid prediluted to 50 mg/mL. Curcumin was obtained from Sigma (St. Louis, Mo.), Lot No. 69H3457. Parthenolide was obtained from Tocris (Ballwin, Mo.) Lot No. 7/18089. DMSO was obtained from Sigma (St. Louis, Mo.), Lot No.80K3695. 0.9% Sodium Chloride for Injection, USP (saline) was manufactured by Abbott Laboratories (Lot No. 55-199-DK). Sterile Water for Injection, USP (WFI) was manufactured by Lyphomed, Inc. (Lot No. 390849).

Formulations: Test preparations (treatment groups) are summarized in Table 4.

For preparation of formulation 1 and 2, amonafide was weighed into vials and dissolved in DMSO at 12.5 mg/mL.

For formulation 3, amonafide was weighed into vials and dissolved in saline.

For formulation 4, the contents of a 10-mg vial of lyophilized CDDP (Cisplatin for Injection) was resuspended with 10 mL WFI to produce a 1 mg/mL CDDP suspension.

For formulation 5, paclitaxel, prediluted in Cremaphor/EL and dehydrated alcohol to 6 mg/mL was further diluted to 3.3 mg/mL with WFI.

Formulation 6 was made by adding 0.9% Sodium Chloride for Injection to a vial of 10 mg of vinblastine lypholized powder.

Formulations 7–10 were prepared by diluting the appropriate amount of each test agent into saline (7-2.5 mg/mL etoposide, 8-7.5 mg/mL 5-fluorouracil, 9-3.75 mg/mL 5-fluorouracil 10-2.5 mg/mL colchicine,).

Formulation 11 was undiluted HHT-Clin, used as received.

Formulations 12 and 13 were prepared by diluting the appropriate amount of each test agent into DMSO (12-6.25 mg/mL curcumin and 13-5 mg/mL parthenolide).

Animals: Female C3H mice (Charles River Laboratories, Holister, Calif.), approximately 3 months old, were used for the study. The average body weight was approximately 25 g. Animals were maintained in isolator cages on a 12-hour light-and-dark cycle. Food and water were available ad libitum.

Tumors: The RIF-1 murine fibrosarcoma cell line was maintained in in vitro culture (Waymouth medium supplemented with 20% fetal bovine serum) at 37° C. in a humidified 5% $CO_2$ incubator. Log-phase RIF-1 cells were trypsinized and harvested from cell culture flasks to yield a concentration of $4 \times 10^6$ cells/mL, then injected intradermally in a volume of 50 $\mu$L (equivalent to $2 \times 10^5$ cells per injection) into both flanks of each mouse. Nine days later, when tumors reached approximately 100 $mm^3$ in size, the animals were randomized to different treatment groups.

Treatment Groups: Treatment groups are summarized in Table 4. Four to five animals were assigned to each treatment group. The intraperitoneal injection volume was 100 $\mu$L. The oral administration volume was 100 $\mu$L. Combination treatments using two test agents were administered as two separate injections, with the second one following the first either immediately or after 30 minutes.

Evaluation of Tumor Growth Delay: Tumors were measured three times weekly for up to 22 days with Vernier calipers. Tumor volume (cubic millimeters, $mm^3$) was calculated according to the formula:

$$V = \pi/6 \times D_1 \times D_2 \times D_3$$

in which $D_{1-3}$ are perpendicular diameters measured in millimeters (mm).

Tumor volume quadrupling time (TVQT), defined as the time required for a tumor to grow to four times (4x) its initial volume (at the time of treatment), was used as a study endpoint. The TVQT was determined for each treatment group and expressed in days as the mean ±standard error (SE).

Antitumor activity or modulation of tumor growth (as measured by delayed tumor growth, i.e. increases in TVQT values) by amonafide administered as a single agent or in combination with other chemotherapeutics is presented in Table 5.

Results from five separate experiments are included in this study. Untreated control animals quadrupled in size in an average of 7.0 days. Intraperitoneal administration of amonafide-NCI formulated in DMSO at 50 mg/Kg had a TVQT of 9.7 days. The additional intraperitoneal administration of CDDP further extended the mean TVQT to 17.9 days. Intraperitoneal administration of amonafide-Penta formulated in DMSO at 50 mg/Kg had a TVQT of 9.3 days. While paclitaxel (10 mg/Kg), alone, demonstrated a TVQT of 7.9 days, the addition of amonafide (50 mg/kg) extended the TVQT to 9.8 days.

Amonafide-Penta formulated in saline at 30 mg/Kg was used for the remainder of the combination studies.

At 30 mg/Kg, amonafide had an average TVQT of 7.3 days. Combination administration of cisplatin (4 mg/Kg) with amonafide (30 mg/Kg) yielded a TVQT of 11.0 days, which was greater than amonafide (TVQT=7.3 days) or cisplatin (TVQT=9.2 days), alone.

Administration of amonafide (30 mg/Kg) in combination with 5-fluorouracil (30 mg/Kg) resulted in a TVQT of 20.2 days versus 13.6 days for 5-fluorouracil, alone. At a dose of 15 mg/Kg, 5-fluorouracil gave a TVQT of 6.7 days versus 7.7 days when it was combined with amonafide at 30 mg/Kg. Combination administration of amonafide (30 mg/Kg) and vinblastine (2 mg/Kg) yielded a TVQT of 9.5 days versus 8.6 days for vinblastine, alone. Combination administration of amonafide (30 mg/Kg) and homoharringtonine (4 mg/Kg) yielded a TVQT of 10.2 days, versus 8.5 for homoharringtonie, alone. Amonafide in combination with etoposide(10 mg/Kg) gave a TVQT of 8.5 days which was the same as the TVQT for etoposide, alone. Combinations of amonafide with curcumin or parthenolide yielded TVQT's of 8.2 days and 7.6 days, respectively, which was less than curcumin (TVQT=9.7 days) or parthenolide (TVQT=8.5) as individual agents.

Orally administered colchicine (10 mg/Kg) yielded a TVQT of 6.3 days. Amonafide in combination with colchicine increased the TVQT to 7.1 days.

There were animal deaths in some groups that were recorded as follows: Two of four mice died after treatment of amonafide-NCI formulated in DMSO at 12.5 mg/mL.

In summary, intraperitoneal administration of amonafide had antitumor activity in the RIF-1 murine fibrosarcoma tumor model. Intraperitoneal administration of amonafide in combination with cisplatin, paclitaxel, vinblastine, 5-fluorouracil and homoharringtonine had antitumor activity levels greater than amonafide alone, or the individual test agents. The best combinatorial activities used cisplatin, 5-fluorouracil, and homharringtonine. Amonafide in combination with colchicine had antitumor activity less than amonafide alone. Amonafide in combination with etoposide, curcumin or parthenolide was greater than that of amonafide alone, but less than that of the test agents, individually.

TABLE 4

Summary of Treatment Groups

| Formulation | Treatment | Concentration (mg/mL) | Route of Administration | Injection Volume (µL) |
|---|---|---|---|---|
| 1 | Amonafide-NCI in DMSO | 12.5 | IP | 100 |
| 2 | Amonafide-Penta in DMSO | 12.5 | IP | 100 |
| 3 | Amonafide-Penta in Saline | 7.5 | IP | 100 |
| 4 | CDDP in WFI | 1 | IP | 100 |
| 5 | Paclitaxel in WFI | 2.5 | IP | 100 |
| 6 | Vinblastine in saline | 0.5 | IP | 100 |
| 7 | Etoposide in saline | 2.5 | IP | 100 |
| 8 | 5-Fluorouracil in saline | 3.75 | IP | 100 |
| 9 | 5-Fluorouracil in saline | 7.5 | IP | 100 |
| 10 | Colchicine in saline | 2.5 | PO | 100 |
| 11 | HHT-Clin in WFI | 1 | IP | 100 |
| 12 | Curcumin in DMSO | 6.25 | IP | 100 |
| 13 | Parthenolide in DMSO | 5 | IP | 100 |

TABLE 5

Effect of Amonafide and Amonafide in Combination with Other Chemotherapeutics on RIF-1 Tumor Growth in C3H Mice

| Group | Treatment | Drug Dose (mg/Kg) | Route of Administration | Number of Tumors | TVQT |
|---|---|---|---|---|---|
| 1 | Untreated Control | — | — | 40 | 7.0 ± 0.2 |
| 2 | Amonafide-NCI/DMSO | 50 | IP | 8 | 9.7 ± 0.6 |
| 3 | Amonafide-Penta/DMSO | 50 | IP | 8 | 9.3 ± 0.3 |
| 4 | Amonafide-Penta/Saline | 30 | IP | 12 | 7.3 ± 0.2 |
| 5 | Cisplatin/WFI | 4 | IP | 16 | 9.2 ± 0.4 |
| 6 | Paclitaxel/CremaphorEL | 10 | IP | 8 | 7.9 ± 0.3 |
| 7 | Vinblastine/Saline | 2 | IP | 8 | 8.6 ± 0.4 |
| 8 | Etoposide/Saline | 10 | IP | 8 | 8.5 ± 0.5 |
| 9 | Fluorouracil/Saline | 15 | IP | 8 | 6.7 ± 0.4 |
| 10 | Fluorouracil/Saline | 30 | IP | 8 | 13.6 ± 1.9 |
| 11 | Homoharringtonine/WFI | 4 | IP | 8 | 8.5 ± 0.5 |
| 11 | Colchicine/Saline | 10 | PO | 8 | 6.3 ± 0.3 |
| 12 | Curcumin/DMSO | 25 | IP | 8 | 9.7 ± 1.1 |
| 13 | Parthenolide/DMSO | 20 | IP | 8 | 8.5 ± 0.8 |
| 14 | Amonafide-NCI/DMSO-30 -CDDP/WFI | 50,4 | IP, IP | 4 | 17.9 ± 0.4 |
| 15 | Amonafide-Penta/Saline-10 sec-CDDP/WFI | 30,4 | IP, IP | 8 | 11.0 ± 0.4 |
| 16 | Amonafide-Penta/DMSO-10 sec- Paclitaxel/Cremaphor EL | 30/10 | IP, IP | 8 | 9.8 ± 0.4 |
| 17 | Amonafide-Penta/Saline-10 sec- Vinblastine/Saline | 30,2 | IP, IP | 8 | 9.5 ± 1.1 |
| 18 | Amonafide-Penta/Saline-10 sec- Etoposide/Saline | 30,10 | IP, IP | 8 | 8.5 ± 0.9 |
| 19 | Amonafide-Penta/Saline -10 sec- 5-Fluorouracil/Saline | 30,15 | IP, IP | 8 | 7.7 ± 0.8 |
| 20 | Amonafide-Penta/Saline-10 sec- 5-Fluorouracil/Saline | 30,30 | IP, IP | 8 | 20.2 ± 1.0 |
| 21 | Amonafide/WFI-10 sec-HHT-Clin/WFI | 30,4 | IP, IP | 8 | 10.2 ± 0.5 |
| 22 | Amonafide-Penta/Saline-10 sec- Colchicine/WFI | 30,10 | IP, PO | 8 | 7.1 ± 0.3 |
| 23 | Amonafide-Penta/Saline-10 sec- Curcumin | 30/25 | IP, IP | 8 | 8.2 ± 0.2 |
| 24 | Amonafide-Penta/Saline-10 sec- Parthenolide | 30/20 | IP, IP | 8 | 7.6 ± 0.3 |

I claim:

1. A method of treatment of a host with a cellular proliferative disease, comprising contacting said host with a naphthalimide comprising an amonafide in conjunction with an antiproliferative agent comprising cisplatin, each in an amount sufficient to modulate said cellular proliferative disease, wherein said cellular proliferative disease is a tumor and said tumor an said tumor is sensitive to the combination and wherein the modulation of said disease with said naphthalimide and said antiproliferative agent is greater than that for said naphthalimide and said antiproliferative agent alone.

2. A method according to claim 1 wherein said naphthalimide is administered before the administration of said antiproliferative agent.

3. A method according to claim 1 wherein said naphthalimide is administered during the administration of said antiproliferative agent.

4. A method according to claim 1 wherein said naphthalimide is administered after the administration of said antiproliferative agent.

5. The method according to claim 1 wherein said tumor is a solid tumor.

6. The method according to claim 5 wherein said modulation comprises the reduction of tumor growth.

7. The method according to claim 5 wherein said modulation comprises inhibition of tumor growth.

8. The method according to claim 5 wherein said modulation comprises an increase in tumor volume quadrupling time.

9. A composition comprising an amonafide and cisplatin.

* * * * *